United States Patent [19]

Karami et al.

[11] 4,427,408
[45] Jan. 24, 1984

[54] DISPOSABLE PANTY AND METHOD

[75] Inventors: Hamzeh Karami, Tilff; Claude Haulait, Romsee; Terence Cooper, Embourg, all of Belgium

[73] Assignee: Colgate-Palmolive Company, New York, N.Y.

[21] Appl. No.: 328,771

[22] Filed: Dec. 8, 1981

[51] Int. Cl.$^3$ .............................................. A41B 9/04
[52] U.S. Cl. .................................. 604/393; 604/385; 2/402; 2/406
[58] Field of Search .............................. 604/393–396, 604/378–380, 385, 370; 2/402, 406; 428/74, 76, 193, 194; 156/163, 226, 229, 291, 292, 308.4

[56] References Cited

U.S. PATENT DOCUMENTS

| | | | |
|---|---|---|---|
| 2,839,058 | 6/1958 | Biever | 604/393 |
| 3,063,452 | 11/1962 | Del Guercio | 604/378 |
| 3,559,648 | 2/1971 | Mason | 604/378 |
| 3,989,867 | 11/1976 | Sisson | 604/370 |
| 4,302,853 | 12/1981 | Mesek | 604/393 |
| 4,324,245 | 4/1982 | Mesek et al. | 604/385 |

*Primary Examiner*—C. Fred Rosenbaum
*Assistant Examiner*—Sherri Vinyard
*Attorney, Agent, or Firm*—Norman Blumenkopf; Herbert S. Sylvester; Murray M. Grill

[57] ABSTRACT

A disposable panty and method of making the disposable panty wherein two panels are positioned so that the facing sheets of each face each other. The panels include absorbent pads between said facing sheets and outer backing sheets. Pairs of elasticized strips are disposed along the sides of said panels, one pair cooperating to form a waistband. The panels are attached to each other along the end edges and at a location medial the end edges and adjacent the other pair of elasticized strips to form thigh bands defining crotch seals.

7 Claims, 11 Drawing Figures

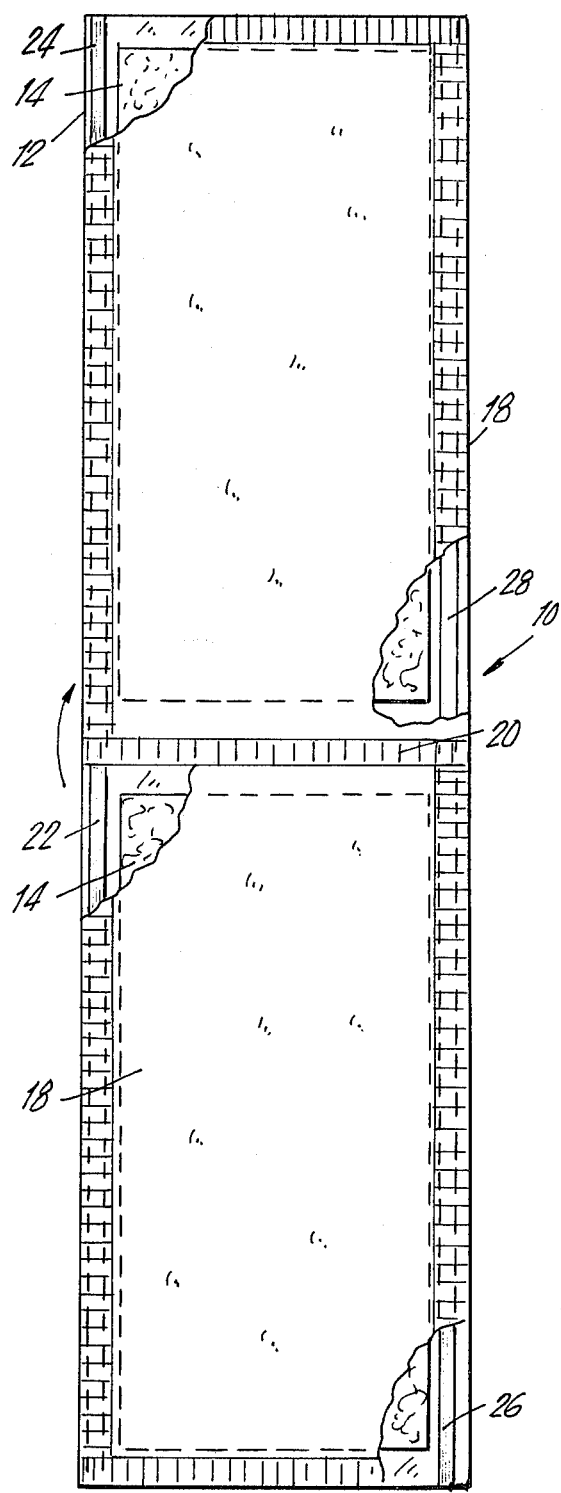
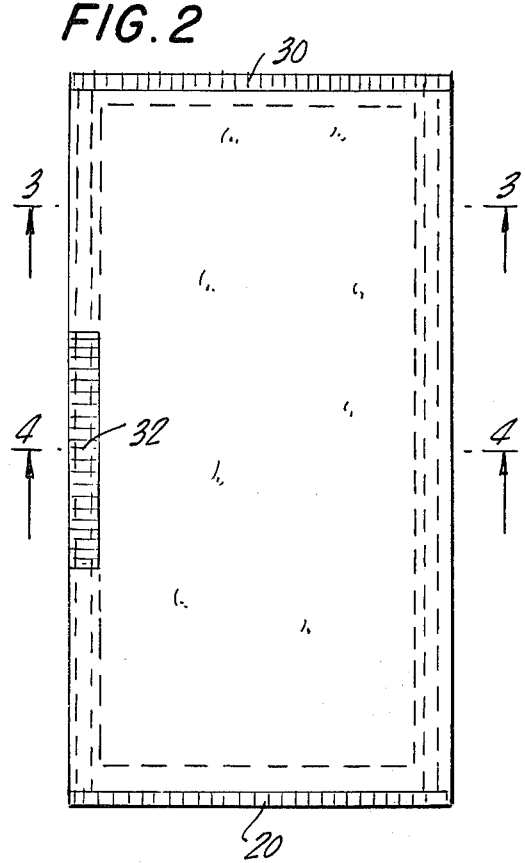
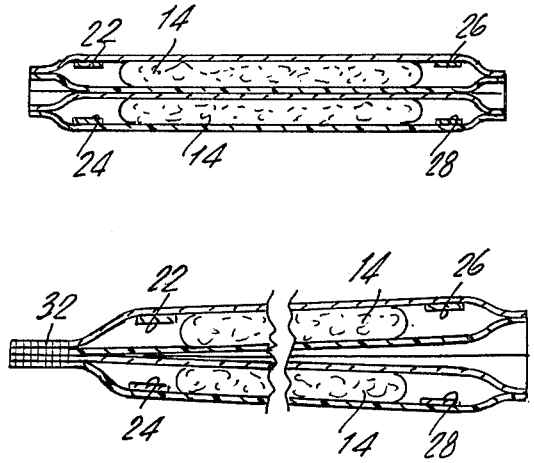

DISPOSABLE PANTY AND METHOD

BACKGROUND OF THE INVENTION

1. Field of the Invention

This invention relates to an elasticized disposable panty and to a method of making an elasticized disposable panty.

2. Description of the Prior Art

In the past elasticized diapers have been developed for use only with contoured shaped configurations such as hour-glass shape such as that disclosed in the U.S. Pat. No. 3,860,003 to Buell, issued Jan. 14, 1975, for "Contractable Side Portions for Disposable Diaper" wherein elastic strips are secured to the crotch portions of the diaper to provide elasticized crotch seals for securement over the legs of the infant to prevent loss of fluid from the interior of the diaper along the legs of the infant.

Elasticized waistbands are common in panties but are not easily capable of being mass produced for use in elasticized diapers because of manufacturing difficulties. Further, contoured diapers are difficult and expensive to manufacture.

Therefore specialized and complicated production equipment is necessitated to contour a diaper and to provide an elasticized waistband for the diaper. Further, diapers so manufactured still require tape fasteners or other securing devices for holding the diaper on the infant or incontinent adult, and require time and technique to assure even a reasonable secure fit.

SUMMARY OF THE INVENTION

The present invention overcomes the disadvantages of prior elasticized diapers by overcoming manufacturing difficulties, eliminating fastening problems providing for both waist and crotch seals, and providing for an inexpensive disposable panty which does not require elaborate cutting for contouring and which is comfortable to the wearer.

In accordance with the invention, an elasticized panty is produced from a two panel configuration wherein one panel is folded over the other and the ends bonded together. Each panel is provided with a facing sheet facing the wearer, an absorbent pad, an impervious backing sheet with pairs of elasticized strips being secured to the sides of said panels. One pair of the elasticized strips forms a waistband for a waist seal and for fitting the diaper on the wearer. The panels are further bonded to each other at a location adjacent each of the other pair of elasticized strips to form thigh bands functioning as crotch seals. The absorbent pads for each panel may be of different thicknesses and additional insert pads may be used as desired.

BRIEF DESCRIPTION OF THE DRAWINGS

FIG. 1 is a plan view of a pair of panels with parts broken away for clarity of the disposable panty during a stage of manufacture thereof;

FIG. 2 is a plan view of the panels after they have been folded;

FIG. 3 is a sectional view taken along the plane of line 3—3 in FIG. 2;

FIG. 4 is a sectional view taken along the plane of line 4—4 in FIG. 2;

DETAILED DESCRIPTION OF THE INVENTION

Figure 5:
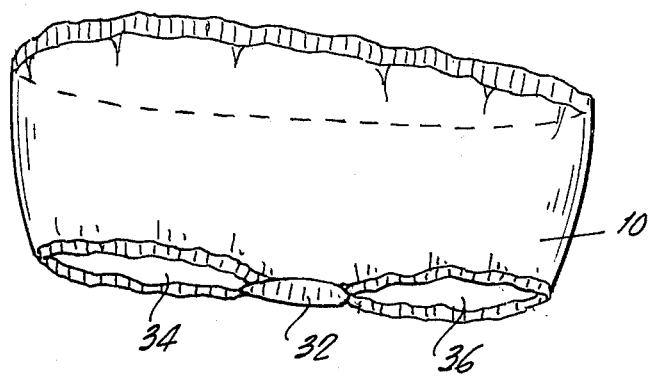
FIG. 5 is a perspective view of a disposable panty according to the invention.

With continuing reference to the accompanying drawings wherein like reference numerals designate similar parts throughout the various views, reference numeral 10 generally designate in FIG. 1 a web from which the panty is manufactured on a conventional diaper machine.

The web 10 includes a backing sheet 12 into which discrete spaced absorbent pads 14 are positioned. These pads 14 may be formed of conventional wood fluff, cotton, or the like, with or without wadding sheets as desired. A facing sheet 16 overlies the pads and is bonded to the backing sheet along the peripheral edges thereof as at 18. The facing sheet is bonded to the backing sheet 12 at 20 between the two pads 14.

The two pads 14 may be of the same of the same or differing thicknesses or materials depending upon the settings of the diaper machine as desired.

Pairs of elasticized strips 22,24 and 26, 28 are bonded by heat sealing, cold melt or hot melt adhesives, or any other bonding means to the backing sheet 12. As shown the elasticized strips are bonded to the inside surface of the backing sheet but the elasticized strips may be bonded, if desired, to the outer surfaces of the backing sheet 12.

After the two panels are formed as shown in FIG. 1 they may be folded along the space 20 between the pads so as to be coextensive and then the free ends are bonded at 30 by sealing, hot or cold melt adhesives or other adhesives as desired.

Preferably, simultaneously at a location 32 medial between the ends 20, 30 of the coextensive panels, the panels are bonded together by heat sealing or suitable adhesives. This, as can be seen best in FIG. 5, defines two thigh receiving openings 34, 36 with the strips 22, 24 defining thigh bands forming crotch seals and the elasticized strips 26, 28 forming a waistband defining a waist seal.

Figure 6:
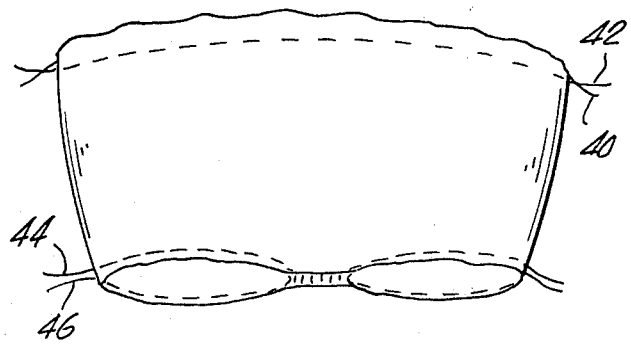
FIG. 6 is a view of a modified form of the invention employing elastic cords.

In FIG. 6 there is shown a modification in which the elasticized strips may be in the form of elastic cords 40, 42, and 44, 46 which may then be adjustably tied for better fit and seal.

Figure 7:
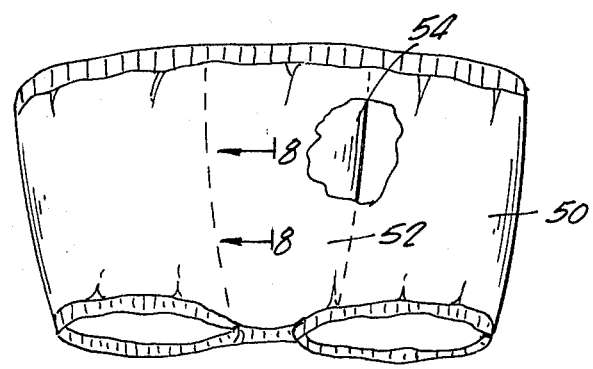
FIG. 7 is a view of a disposable panty employing a double pad.
Figure 8:
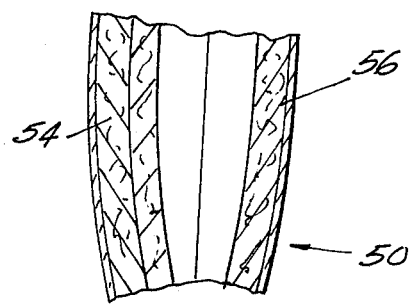
FIG. 8 is a detail view of a disposable panty taken along the plane of line 8—8 in FIG. 7.

Referring now to FIGS. 7 and 8 herein there is shown a panty 50 having one or more additional pads 52 provided which may be specifically located in the crotch area. The pad 52 may have a thick section 54 and a thin section 56 so that the diaper may be reversably fitted depending on the sex of the wearer. The additional pad or pads 52 may be in the form of inserts as desired.

Figure 9:
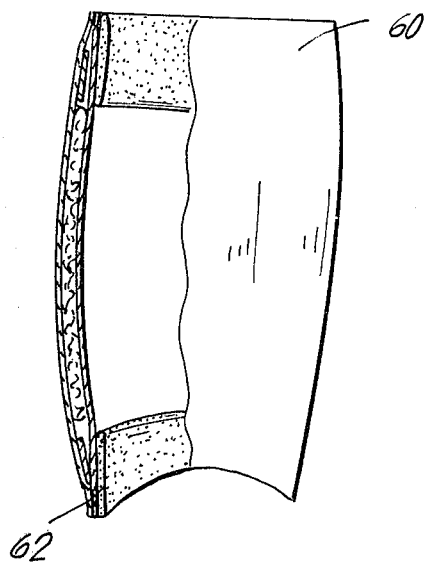
FIG. 9 is a view of an embodiment employing elasticized foam.

As shown in FIG. 9, additional elasticized foam material 60 may be disposed at the waist to provide for a better and more comfortable fit and additional elasticized foam material may be provided at the thighs for better and more comfortable fit.

Figure 10:
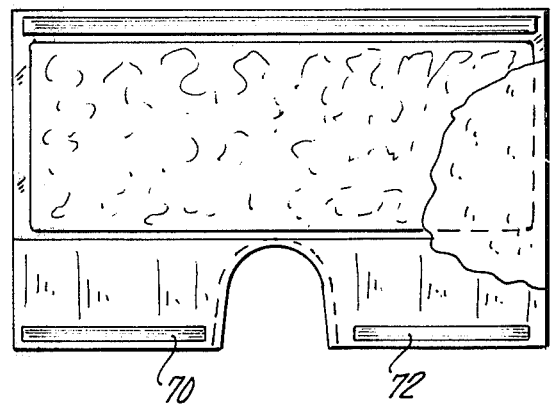
FIG. 10 is a front view of a disposable "Bermuda" panty having extended thigh portions.
Figure 11:
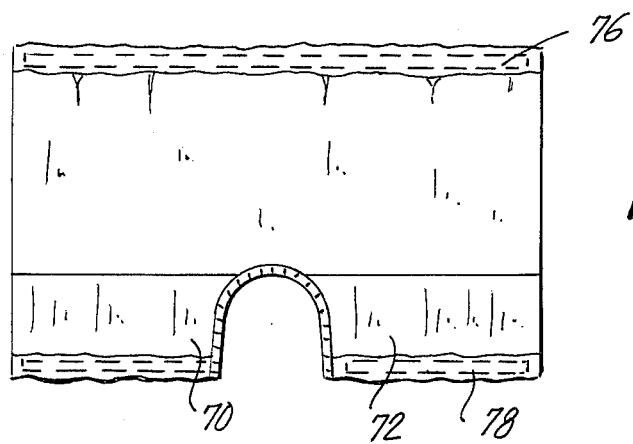
FIG. 11 is a rear view of the diaper shown in FIG. 10.

In FIGS. 10 and 11 there is shown a "Bermuda" panty variation wherein thigh extensions 70 and 72, preferably of elasticized material, may be provided to insure a better seal while also providing a better seal. As shown in FIG. 11, foam material at 76 and 78 may be added at the waist and thighs.

It is possible to utilize stretch materials to insure the diaper fitting wearers of various sizes. Further, the backing sheet may be made breathable as set forth in U.S. Pat. No. 3,989,867. The elastic strips may be stirred for greater efficacy as shown in U.S. Pat. Nos. 3,639,917 and 3,912,651.

What is claimed is:

1. A disposable panty comprising an impervious backing sheet, a facing sheet and a pair of spaced absorbent pads placed between said facing and backing sheets, said facing sheet being bonded to said backing sheet ab out its periphery and between said pads to form front and back panels, said panels being folded between said pads and having their free ends bonded to each other, said panels each having two elasticized strips bonded along the sides thereof, one pair of elasticized strips forming a waist band, said panels being attached to each other at a crotch location medial the ends thereof and adjacent the other pair of elasticized strips to form thigh holes and a pair of crotch seals to extend about the thighs of the wearers.

2. A disposable panty according to claim 1, wherein said absorbent pads are of different thicknesses.

3. A disposable panty according to claim 1, wherein at least one of said backing sheet and facing sheet are of a stretch material.

4. A disposable panty according to claim 1, wherein said backing sheet is breathable.

5. A disposable panty according to claim 1, including thigh extensions secured to the crotch portion of said panty, said thigh extensions being of an elasticized material.

6. A process of making a disposable panty comprising the steps of positioning a pair of absorbent pads in spaced relationship between a facing sheet and a backing sheet, bonding said facing sheet to said backing sheet between said absorbent pads and along the peripheral edges of said facing sheet and said backing sheet to form a pair of panels, folding said panels in overlying relationship to each other with each of said panels having their facing sheets facing each other, said panels being folded along the space between said absorbent pads, said panels having pairs of elasticized strips bonded along the sides thereof, then bonding the free end edges of said panels to each other, and bonding said panels to each other at a crotch location medial the end edges thereof and adjacent one pair of said elasticized strips.

7. A process of making a disposable panty according to claim 6, wherein said panels are simultaneously bonded to each other at said free end edges and at said location by heat sealing.

* * * * *